United States Patent [19]

Rohe et al.

[11] 4,104,313

[45] Aug. 1, 1978

[54] HALOGENATED 4-TRIFLUOROMETHYL-4'-NITRO-DIPHENYL-ETHER

[75] Inventors: Lothar Rohe, Wuppertal; Jürgen Schramm, Dormagen; Erich Klauke, Odenthal-Hahnenberg; Ludwig Eue; Robert Rudolf Schmidt, both of Cologne, all of Germany

[73] Assignee: Bayer Aktiengesellschaft, Leverkusen, Germany

[21] Appl. No.: 686,349

[22] Filed: May 14, 1976

Related U.S. Application Data

[63] Continuation of Ser. No. 483,332, Jun. 26, 1974, abandoned.

[30] Foreign Application Priority Data

Jul. 3, 1973 [DE] Fed. Rep. of Germany ....... 2333848

[51] Int. Cl.[2] ........................ C07C 43/20; C07C 43/28

[52] U.S. Cl. ............................ 260/612 R; 260/609 F; 71/98; 71/124

[58] Field of Search .................................... 260/612 R

[56] References Cited

U.S. PATENT DOCUMENTS

| | | | |
|---|---|---|---|
| 3,798,276 | 3/1974 | Bayer et al | 260/612 R |
| 3,888,932 | 6/1975 | Bayer et al. | 260/612 R |
| 3,928,416 | 12/1975 | Bayer et al. | 260/612 R X |

*Primary Examiner*—Bernard Helfin
*Attorney, Agent, or Firm*—Burgess, Dinklage & Sprung

[57] ABSTRACT

Halogenated 4-trifluoromethyl-4'-nitro-diphenyl-ether compounds of the formula

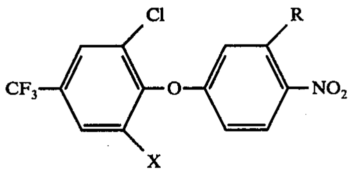

(I)

in which
R is halogen or methylthio, and
X is hydrogen or chlorine, are outstandingly effective as herbicides, particularly as selective herbicides.

1 Claim, No Drawings

HALOGENATED 4-TRIFLUOROMETHYL-4'-NITRO-DIPHENYL-ETHER

This is a continuation of application Ser. No. 483,332, filed June 26, 1974, and now abandoned.

The present invention relates to certain new halogenated 4-trifluoromethyl-4'-nitro-diphenyl-ether compounds, to herbicidal compositions containing them, and to herbicidal applications using them.

It is known that 2,4-dichloro-4'-nitro-diphenyl-ether, sold under the name Nitrofen and disclosed in U.S. Pat. No. 3,080,225, can be used for combating weeds. However, this compound is not active against all weeds, especially if low amounts and low concentrations are used; for example, it has a low activity against species of Echinochloa, such as *Echinochloa crus galli,* which occurs as a weed in rice, and against species of Eleocharis, such as *Eleocharis palustris.*

The present invention provides halogenated 4-trifluoromethyl-4'-nitro-diphenyl-ethers of the formula

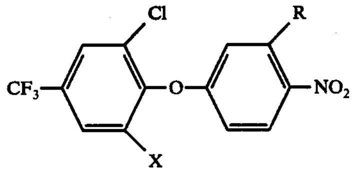

(I)

in which

R is halogen or methylthio, and

X is hydrogen or chlorine (but not hydrogen when R is chlorine).

Surprisingly, the halogenated 4-trifluoromethyl-4'-nitro-diphenyl-ethers according to the invention display a substantially greater herbicidal action than the closest compound previously known in the art, 2,4-dichloro-4'-nitro-diphenyl ether. The compounds according to the invention thus represent an enrichment of the art.

The invention also provides a process for the production of a halogenated 4-trifluoromethyl-4'-nitro-diphenyl-ether of the formula (I) in which (a) a 4-halobenzotrifluoride of the formula

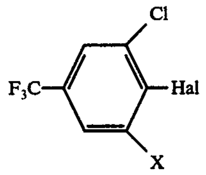

(II)

in which

X has the above-mentioned meaning and

Hal is halogen, is reacted sith a phenolate of the formula

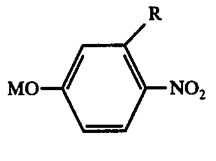

(III)

in which

R has the above-mentioned meaning and

M is an alkali metal, optionally in the presence of an aprotic solvent; or (if R in formula (I) does not represent methylthio)

(b) a diphenyl-ether of the formula

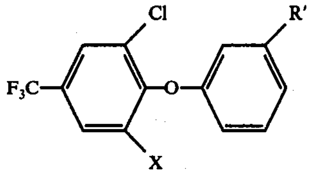

(IV)

in which

X has the above-mentioned meaning and

R' is halogen, is reacted with a nitrating agent;

or (if R in formula (I) represents methylthio)

(c) a diphenyl-ether of the formula

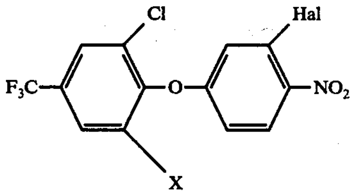

(V)

in which

X has the above-mentioned means and

Hal is halogen, is reacted with a methylmercaptide in the presence of a diluent.

If, in accordance with process variant (a), 3,4,5-trichlorobenzotrifluoride and sodium m-chloro-p-nitrophenolate are used as starting compounds, the course of the reaction can be represented by the following formula scheme:

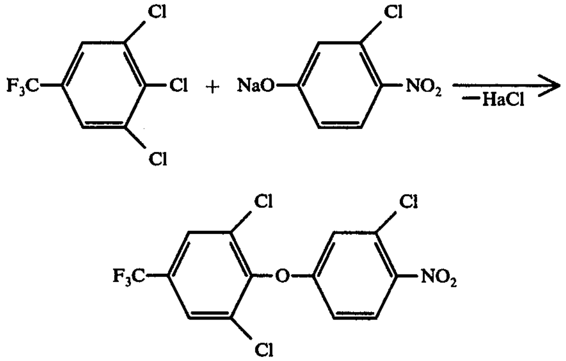

If, according to process variant (b), 2,3'-dichloro-4-trifluoromethyl-diphenyl-ether and concentrated nitric acid are used as starting compounds, the course of the reaction can be represented by the following formula scheme:

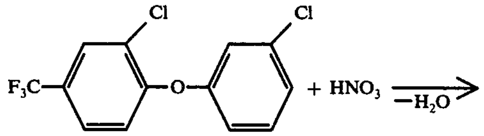

-continued

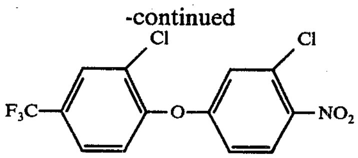

If, according to process variant (c), 2,6-dichloro-4-trifluoromethyl-3'-fluoro-4'-nitro-diphenyl-ether and sodium methylmercaptide are used as starting compounds the course of the reaction can be represented by the following formula scheme:

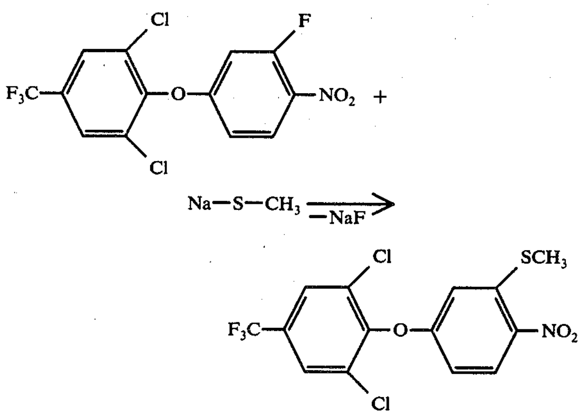

Many of the 4-halobenzotrifluorides (II) and phenolates (III) used as starting compounds for reaction variant (a) are known; any which are not yet known can be prepared according to known methods (some of which are illustrated in the Examples).

All aprotic solvents can be used as diluents in carrying out process variant (a). Preferred ones include amides, such as hexamethylphosphoric acid triamide, dimethylformamide or dimethylacetamide and also sulfoxides, such as dimethylsulfoxide, as well as ketones, such as methyl ethyl ketone, and nitriles, such as acetonitrile.

In process variant (a), the reaction temperatures can be varied over a wide range. In general, the reaction is carried out at 40° to 200° C, preferably at 80° to 160° C.

The starting compound of the formulae (II) and (III) used in process variant (a) are preferably reacted in stoichiometric amounts, but amounts greater or less than this by up to 20% can be used without significant losses in yield. The reaction mixture may be worked up in the manner customary in the laboratory.

The diphenyl-ethers of the formula (IV) used as the starting compounds in process variant (b) are not yet known. However, they can be obtained in a manner analogous to the abovementioned process variant (a) by reaction of 4-halobenzotrifluorides with phenolates ("Williamson ether synthesis"), if appropriate in the presence of an aprotic solvent (compare, on this matter, the data in the Examples).

The nitrating agents required for the nitration reaction according to process variang (b) are generally known. Thus, for example nitric acid diluted with glacial acetic acid, or a mixture of potassium nitrate and sulfuric acid, or a sulfuric acid/nitric acid mixture, can be used.

Diluents which can be used in process variant (b) are preferably acids or acid anhydrides such as glacial acetic acid, acetic anhydride or dilute sulfuric acid. However, it is also possible to work without a diluent.

The reaction temperatures can also be varied in the case of process variant (b). In general, the reaction is carried out at −20° to +100° C, preferably at −15° to +70° C.

The nitrating agents used in process variant (b), such as concentrated nitric acid and potassium nitrate, are preferably used in two-fold to five-fold excess. The isolation of the reaction products may be carried out in a generally known manner.

Process variant (c) belongs to a type of process which has in principle been known for a considerable time.

The diphenyl-ethers of the formula (V) used as starting compounds in the process variant (c) are not known. However, like the diphenyl-ethers of the formula (IV), they can be obtained in a manner analogous to the above-mentioned process variant (a) (by "Williamson ether synthesis").

Possible diluents for use in carrying out process variant (c) are aprotic polar solvents such as acetone, acetonitrile, dimethylformamide and dimethylsulfoxide.

The reaction temperatures can also be varied considerably in process variant (c). In general, the reaction is carried out at 10° to 120° C, preferably at 20° to 100° C.

In carrying out process variant (c), the reactants are preferably employed in equimolar amounts. Working up may be effected in customary manner.

EXAMPLE 1 — Preparation of 2,3',6-trichloro-4-trifluoromethyl-4'-nitrodiphenyl-ether Process variant (b):

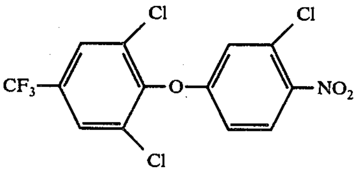
(1)

1,364 g (4 mols) of 2,3'-6-trichloro-4-trifluoromethyl-diphenyl-ether were dissolved in 2,500 ml of acetic anhydride. A mixture of 497 g of nitric acid (d = 1.4) and 512 g of concentrated sulfuric acid was added dropwise thereto over the course of two-and-a-half hours at 0°-5° C. After the dropwise addition, the mixture was stirred for a further two hours at 5° C. The reaction mixture was then diluted with four liters of methylene chloride and poured into approximately four liters of ice water. The organic phase was washed twice with four liters of water at a time and dried over sodium sulfate. The solvent was stripped off in vacuo and the residue was freed of volatile constituents on a steam jet apparatus at 120° C. 1,433 g (92.5% of theory) of 2,3'-6-trichloro-4-trifluoromethyl-4'-nitrodiphenyl-ether were obtained as a red oil of refractive index $n_D^{23}$: 1.5078.

The following were prepared analogously to Example 1:

EXAMPLE 2 — Preparation of 2,6-dichloro-3′-fluoro-4-trifluoromethyl-4′-nitrodiphenyl-ether

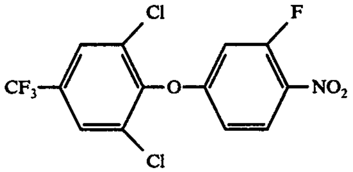

(2)

This compound had a refactive index $n_D^{23}$: 1.5608.

EXAMPLE 3 — Preparation of 2-chloro-3′-fluoro-4-trifluoromethyl-4′-nitrodiphenyl ether

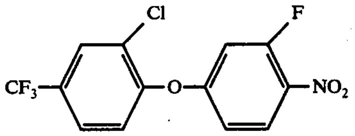

(3)

This compound had a refractive index $n_D^{23}$: 1.5489.

Preparation of the intermediates for Examples 1, 2 and 3:

Variant (a):

606 g (4 mols) of sodium 3-chlorophenolate were dissolved in 5 liters of dimethylsulfoxide and the solution was warmed to 120° C. 1,000 g (4 mols) of 3,4,5-trichlorotrifluoromethylbenzene were added dropwise at this temperature over the course of two hours and the mixture was stirred for a further six hours at 160° C. The solvent was distilled off in vacuo. The residue was poured into water and the mixture was extracted with two liters of methylene chloride. The organic phase was washed once with two liters of water, once with 5% strength sodium hydroxide solution and then again with water. After drying the organic phase with sodium sulfate, the solvent was stripped off and the residue was distilled. 860 g of 2,3′,6-trichloro-4-trifluoromethyl-diphenyl-ether (63% of theory) were obtained, of boiling point: 134°-138° C at 3 mm Hg, and refractive index $n_D^{22}$: 1.5418.

The following were prepared analogously:

2,6-Dichloro-3-fluoro-4-trifluoromethyl-diphenyl ether, $n_D^{23}$: 1.5270.

2-Chloro-3′-fluoro-4-trifuoromethyl-diphenyl-ether, $n_D^{23}$: 1.5263.

Preparation of the starting material:

3,4,5-Trichlorobenzotrifluoride, required as the intermediate product, was obtained in a manner which is in principle known (see J. Am. Chem. Soc. 57, 2066–2068 (1935) and U.S. Pat. No. 2,654,789) by reaction of 4-chloro-benzotrifluoride with chlorine in the presence of 10 mol % of ferric (iron-III) chloride; for this purpose, chlorine was passed into the reaction mixture, at a temperature of 60°-160° C, while stirring and using reflux cooling, until the refractive index of the reaction mixture had risen to $n_D^{20}$ = 1.5025. The mixture was worked up as follows: the catalyst was filtered off and the reaction mixture was distilled through a bridge. The distillate was rectified using a 1 m long silver-jacketed column. In addition to 3,4-dichlorobenzotrifuoride of refractive index $n_D^{20}$ = 1.4758 and boiling point 172°-175° C, a 3,4,5- and 2,4,5-trichlorobenzotrifluoride isomer mixture of refractive index $n_D^{20}$ = 1.5015 was obtained. This mixture was separated by a further vacuum distillation through a silver-mirror-coated packed column (1.25 m height, with Wilson glass spiral packings of 3 mm diameter), a magnetic vapor distributor with a time interval swith serving as the column head. A vacuum of 50 mm Hg was applied at the column head; the bath temperature was 142°-150° C and the reflux ration was 60:1. 3,4,5-Trichlorobenzotrifluoride was then collected at a temperature of 113° C. It was characterized by the NMR spectrum; the compound has a singlet at 7.65 ppm (at 60 MHz, measured in carbon tetrachloride as the solvent).

EXAMPLE 4 — Preparation of 2,6-dichloro-4-trifluoromethyl-4′-nitro-3′-methyl-thiodiphenyl-ether Process variant (c):

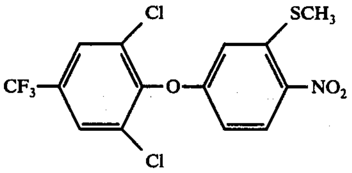

(4)

23 g (0.0635 mol) of 2,6-dichloro-3′-fluoro-4-trifluoromethyl-4′-nitrodiphenyl-ether were dissolved in 100 ml of acetonitrile and 4.45 g (0.0635 mol) of sodium methylmercaptide were added. When the slightly exothermic reaction had subsided, the reaction mixture was warmed to 80° C for four hours. After cooling, it was poured into 500 ml of water, whereupon the reaction product was obtained as a solid. This was filtered off, dried and recrystallized from acetonitrile. 6.5 g of 2,6-dichloro-4-trifluoromethyl-4′-nitro-3′-methyl-thiodiphenyl-ether of melting point 135° C (26% of theory) were obtained.

EXAMPLE 5 — Preparation of 2-Chloro-4-trifluoromethyl-4′-nitro-3′-methylthio-diphenyl-ether

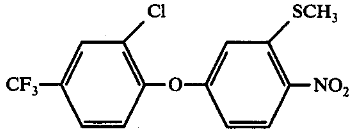

(5)

2-Chloro-4-trifluoromethyl-4′-nitro-3′-methylthiodiphenyl-ether was prepared analogously to Example 4 by reaction of 2-chloro-3′-fluoro-4-trifluoromethyl-4′-nitrodiphenyl-ether (Example 3) with Na methylmercaptide; melting point 95° C (recrystallized from ethanol).

The active compounds according to the invention have excellent herbicidal properties and can therefore be used for combating weeds.

Weeds in the broadest sense are plants which grow in locations where they are not desired. As weeds there may be mentioned: dicotyledons, such as mustard (Sinapis), cress (Lepidum), cleavers (Galium), chickweed (Stellaria), camomile (Matricaria), gallant Soldier (Galinsoga), goosefoot (Chenopodium), annual nettle (Urtica) and groundsel (Senecio), and monocotyledons, such as timothy (Phleum), bluegrass (Poa), fescue (Festuca), goosegrass (Eleusine), foxtail (Setaria), ryegrass (Lolium) and barnyard grass (Echinochloa).

The active compounds according to the invention have a very strong influence on plant growth, but in different ways, so that they can be used as selective herbicides. They display particular advantages as selective herbicides in the cultivation of cotton, rice, carrots and cereals (including maize). In higher concentrations (approximately 10 to 20 kg/ha), they can be employed as total weedkillers.

The active compounds according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents, and/or foam-forming agents. In the case of the use of water as an extender, orgainic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, choroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sufloxide or acetonitrile, as well as water.

By liquefied gaseous diluents or carriers are meant liquids which would be gaseous at normal temperatures and pressures, e.g. aerosol propellants, such as halogenated hydrocarbons, e.g. freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and emulsifiers, such as polyoxyethylene-fatty acid esters, polyoxyethylene-fatty alcohol ethers, for example alkylarylpolyglycol ethers, alkyl sulfonates, alkyl sulfates and aryl sulfonates as well as albumin hydrolyzation products; and preferred examples of dispersing agents include lignin, sulfite waste liquors and methyl cellulose.

The active compounds according to the invention can be used as a mixture with other active compounds.

The formulations in general contain from 0.1 to 95 percent by weight of active compound, preferably 0.5 to 90 percent by weight.

The active compounds can be used as such or in the form of their formulations or the application forms prepared therefrom, such as ready-to-use solutions, emulsions, suspensions, powders, pastes and granules. They may be applied in the customary manner, for example by watering, spraying, atomizing, sprinkling and dusting.

They can be applied both post-emergence and preemergence; they are preferably applied after emergence of the plants.

The amount of active compound employed can vary within wide ranges. It depends essentially on the nature of the desired effect. In general, the amounts used are 0.1 to 25 kg/ha, preferably 0.5 to 10 kg/ha.

The compounds according to the invention also have an insecticidal, acaricidal and fungicidal action which deserves mention.

The invention therefore provides a hebicidal composition containing as active ingredient a compound according to the invention in admixture with a solid or liquefied gaseous diluent or carrier or in admixture with a liquid diluent or carrier containing a surface-active agent.

The invention also provides a method of combating weeds which comprises applying to the weeds or their habitat a compound according to the invention alone or in the form of a composition containing as active ingredient a compound according to the invention in admixture with a diluent or carrier.

The invention also provides means of providing crops protected from damage by weeds by being grown in areas in which, immediately prior to and/or during the time of the growing, a compound according to the invention was applied alone or in admixture with a diluent or carrier. It will be seen that the usual methods of providing a harvested crop may be improved by the present invention.

The compounds according to the invention, and the preparation and use of the compounds according to the invention, are illustrated by the following Examples. The compounds tested in Examples A and D are identified by the following list.

List of Test Compounds (1) = 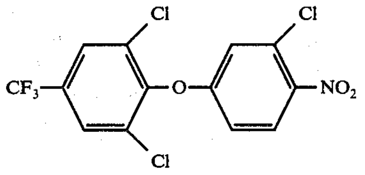

(2) = 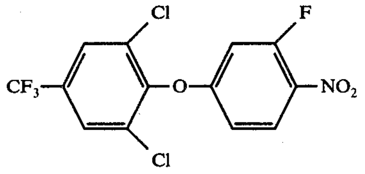

(3) = 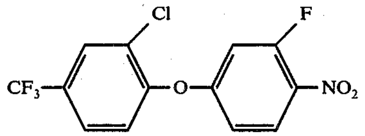

(4) = 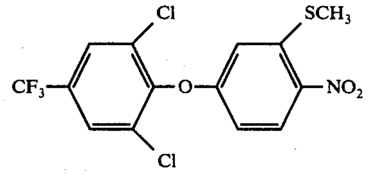

(5) = 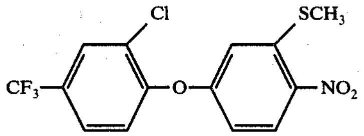

-continued

List of Test Compounds

Nitrofen (known) =

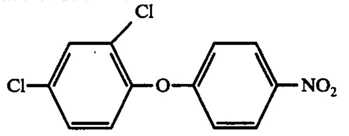

EXAMPLE A

Pre-emergence test

Solvent: 5 parts by weight of acetone

Emulsifier: 1 part by weight of alkylaryl polyglycol ether

To produce a suitable preparation of active compound, one part by weight of active compound was mixed with the stated amount of solvent, the stated amount of emulsifier was added and the concentrate was then diluted with water to the desired concentration.

Seeds of the test plants were sown in normal soil and, after twenty-four hours, watered with the preparation of the active compound. It was expedient to keep constant the amount of water per unit area. The concentration of the active compound in the preparation was of no importance, only the amount of active compound applied per unit area being decisive. After three weeks, the degree of damage to the test plants was determined in % damage in comparison to the development of the untreated control.

0% denotes untreated control

100% denotes total destruction

The active compounds, the amounts applied and the results can be seen from Table A.

Table A

| | | Pre-emergence test | | | | | | | | | |
|---|---|---|---|---|---|---|---|---|---|---|---|
| Active compound | Amount of active compound used, kg/mm | Echinochlea | Chenopodium | Iolium | Stellaria | Calinsoga | Matricaria | Polygonum | Cotton | Wheat | Maize |
| | 5 | 100 | 100 | 100 | 100 | 100 | 100 | 100 | 20 | 100 | 40 |
| (1) | 2.5 | 100 | 80 | 100 | 100 | 100 | 100 | 100 | 20 | 100 | 20 |
| | 1.25 | 100 | 80 | 100 | 80 | 100 | 100 | 100 | 0 | 100 | 0 |
| | 5 | 100 | 100 | 100 | 100 | 100 | 100 | 100 | 80 | 80 | 40 |
| (2) | 2.5 | 100 | 100 | 100 | 100 | 100 | 100 | 100 | 80 | 80 | 20 |
| | 1.25 | 100 | 100 | 100 | 90 | 100 | 100 | 100 | 60 | 80 | 0 |
| | 5 | 100 | 100 | 100 | 100 | 100 | 100 | 100 | 60 | 100 | 80 |
| (3) | 2.5 | 100 | 100 | 100 | 100 | 100 | 100 | 100 | 40 | 100 | 80 |
| | 1.25 | 100 | 100 | 100 | 80 | 100 | 100 | 100 | 0 | 90 | 60 |
| | 5 | 80 | 80 | 100 | 100 | 100 | 100 | 100 | 0 | 60 | 0 |
| (4) | 2.5 | 60 | 80 | 90 | 100 | 100 | 100 | 100 | 0 | 40 | 0 |
| | 1.25 | 60 | 60 | 90 | 80 | 80 | 90 | 100 | 0 | 30 | 0 |
| | 5 | 100 | 100 | 100 | 100 | 100 | 100 | 100 | 60 | 60 | 60 |
| (5) | 2.5 | 100 | 80 | 80 | 80 | 100 | 100 | 100 | 40 | 60 | 40 |
| | 1.23 | 90 | 60 | 80 | 80 | 90 | 100 | 100 | 0 | 60 | 40 |
| Nitrofem | 5 | 100 | 60 | 100 | 20 | 90 | 80 | 90 | 40 | 60 | 60 |
| (known) | 2.5 | 100 | 40 | 90 | 0 | 80 | 80 | 60 | 20 | 40 | 40 |
| | 1.25 | 100 | 20 | 80 | 0 | 60 | 60 | 40 | 0 | 20 | 40 |

EXAMPLE B

Post-emergence test

Solvent: 5 parts by weight of acetone

Emulsifier: 1 part by weight of alkylaryl polyglycol ether

To produce a suitable preparation of active compound, one part by weight of active compound was mixed with the stated amount of solvent, the stated amount of emulsifier was added and the concentrate was then diluted with water to the desired concentration.

Test plants which had a height of 5–15 cm were sprayed with the preparation of the active compound in such a way as to apply the amounts of active compound per unit area which are indicated in the table.

Depending on the concentration of the spray liquor, the amount of water used was between 1,000 and 2,000 liters/ha. After three weeks, the degree of damage to the plants was determined in % damage in comparison to the development of the untreated control 0% denotes untreated control 100% denotes total destruction The active compounds, the amounts used and the results can be seen from Table B.

Table B

| | | Post- emergence test | | | | | | | | | |
|---|---|---|---|---|---|---|---|---|---|---|---|
| Active compound | Amount of active compound used kg/mm | Echinochloa | Chenopodium | Sitapis | Calinsoga | Stellaria | Urtica | Matricaria | Avena fatua | Cotton | Wheat | Carrots |
| (1) | 1 | 100 | 100 | 90 | 100 | 100 | 100 | 100 | 100 | 100 | 100 | 0 |
| | 0.5 | 90 | 100 | 80 | 100 | 100 | 100 | 80 | 100 | 100 | 100 | 0 |
| (2) | 1 | 100 | 100 | 100 | 100 | 100 | 100 | 100 | 100 | 100 | 100 | 0 |
| | 0.5 | 100 | 100 | 100 | 100 | 100 | 100 | 100 | 100 | 100 | 100 | 0 |
| (3) | 1 | 100 | 100 | 100 | 100 | 90 | 100 | 100 | 100 | 100 | 100 | 0 |
| | 0.5 | 100 | 100 | 100 | 100 | 80 | 100 | 90 | 100 | 100 | 100 | 0 |
| (4) | 1 | 100 | 100 | 100 | 100 | 100 | 100 | 100 | 100 | 100 | 100 | 0 |
| | 0.5 | 90 | 100 | 100 | 100 | 100 | 100 | 100 | 80 | 100 | 80 | 0 |
| (5) | 1 | 90 | 100 | 100 | 100 | 100 | 100 | 100 | 100 | 80 | 100 | 0 |
| | 0.5 | 80 | 100 | 100 | 80 | 80 | 100 | 100 | 90 | 80 | 90 | 0 |
| Nitrofen | 1 | 80 | 60 | 20 | 20 | 0 | 100 | 20 | 60 | 100 | 20 | 0 |
| (known) | 0.5 | 60 | 60 | 0 | 20 | 0 | 100 | 20 | 60 | 80 | 20 | 0 |

It will be understood that the specification and examples are illustrative but not limitative of the present invention and that other embodiments within the spirit and scope of the invention will suggest themselves to those skilled in the art.

What is claimed is:

1. Halogenated 2,6-dichloro-3′-fluoro-4-trifluoromethyl-4′-nitrodiphenyl-ether.

* * * * *